United States Patent
Jefferies et al.

(10) Patent No.: US 11,197,832 B2
(45) Date of Patent: *Dec. 14, 2021

(54) CURCUPHENOL COMPOUNDS FOR INCREASING MHC-I EXPRESSION

(71) Applicant: CAVA HEALTHCARE INC., Vancouver (CA)

(72) Inventors: Wilfred Jefferies, Surrey (CA); Reinhard Gabathuler, Montreal (CA); Raymond Andersen, Vancouver (CA); Lilian Nohara, Vancouver (CA); David Williams, Vancouver (CA)

(73) Assignee: Cava Healthcare Inc., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/998,072

(22) Filed: Aug. 20, 2020

(65) Prior Publication Data
US 2020/0375917 A1  Dec. 3, 2020

Related U.S. Application Data

(63) Continuation of application No. 15/415,291, filed on Jan. 25, 2017, now Pat. No. 10,751,296, which is a continuation of application No. 14/548,726, filed on Nov. 20, 2014, now abandoned.

(60) Provisional application No. 61/906,817, filed on Nov. 20, 2013.

(51) Int. Cl.
| | | |
|---|---|---|
| *A61K 31/045* | (2006.01) | |
| *A61K 31/05* | (2006.01) | |
| *A61N 5/10* | (2006.01) | |
| *A61K 31/12* | (2006.01) | |
| *A61K 45/06* | (2006.01) | |

(52) U.S. Cl.
CPC ............ *A61K 31/045* (2013.01); *A61K 31/05* (2013.01); *A61K 31/12* (2013.01); *A61K 45/06* (2013.01); *A61N 5/10* (2013.01); *A61K 2300/00* (2013.01)

(58) Field of Classification Search
CPC ...... A61K 31/05; A61K 31/12; A61K 31/045; A61K 45/06; A61P 35/00; A61P 35/02; A61P 35/04; A61N 5/10
See application file for complete search history.

(56) References Cited

U.S. PATENT DOCUMENTS

| | | |
|---|---|---|
| 2006/0148908 A1 | 7/2006 | Park et al. |
| 2011/0008465 A1 | 1/2011 | Legault et al. |

FOREIGN PATENT DOCUMENTS

| | | |
|---|---|---|
| WO | 2002/083114 | 10/2002 |
| WO | 2015/077411 | 5/2015 |

OTHER PUBLICATIONS

Brahmer et. al., J. Clin. Oncolog., publ. May 20, 2013, vol. 31, No. 15 supplemental, Abstract 8030 (Year: 2013).*
Rodriguez, "Know the Most Common Types of Cancer", Everyday Health, publ. online Feb. 8, 2010, pp. 1-13 (Year: 2010).*
Wistuba et. al., Nature Rev., Clin. Oncology, (2011), vol. 8, pp. 135-141 (Year: 2011).*
Bhatia et. al., Nature Biotechnology, (2012), vol. 30(7), pp. 604-610 (Year: 2012).*
Behery, F. et al., "Mannich-and Lederer-Manasse-based analogues of the natural product S-(+)-curcuphenol as cancer proliferation and migration inhibitors," Medchemcomm, 3(10):1309-1315 (2012).
Chang, C. C. et al., "HLA class I defects in malignant lesions: What have we learned?", Keio J. Med., 52:220-229 (2003).
Choi, M-A et al., "Xanthorrhizol, a natural sesquiterpenoid from Curcuma xanthorrhiza, has an antimetastatic potential in experimental mouse lung metastasis model," Biochemical and Biophysical Research Communications, 326(1):210-217 (2004).
Dall'Acqua et al., Bioorgani & Medicinal Chemistry, 2011, Elsevier, vol. 19, pp. 5876-5885 (Year: 2011).
Delp et al., Bone Marrow Transplantation, 2000, Macmillan Publ Ltd, vol. 25 (suppl 2), pp. S88-S95 (Year: 2000).
Green, J. et al., "An Oxidative Dearomatization-Induced [5+2] Cascade Enabling the Syntheses of α-Cedrene, α-Pipitzol, and sec-Cedrenol," Journal of American Chemical Society, 2011, 133, pp. 1603-1608.
Gul, W. et al., "Chemical transformation and biological studies of marine sesquiterpene (S)-(+)-curcuphenol and its analogs," Biochimica et Biophysical Acta, 1770(11):1513-1519 (2007).
Hewitt, E. W., "The MHC class I antigen presentation pathway: strategies for viral immune evasion," Immunology, 110(2):163-169 (2003).
International Search Report and Written Opinion for International Application No. PCT/US2014/066543, dated Mar. 18, 2015, 12 pages.
Office Action issued for CN Application No. 201480072728.3, dated Mar. 21, 2019, 6 pages, English translation.
Office Action issued for JP Application No. 20145-533609, dated Sep. 10, 2018, 8 pages, English translation.
Patani et al., Chemical Reviews, 1996, American Chemical Society, vol. 96, pp. 3147-3176.
Redondo et al., Cancer Research, 1991, American Association for Cancer, vol. 51, pp. 2463-2468.
Rodrigo, G. et al., "Antiproliferative effects of curcuphenol, a sesquiterpene phenol," Fitoterapia, 81(7):762-766 (2010).
Tasdemir, D. et al., "Bisabolane type sesquiterpenes from a marine didiscus sponge," Turk. J. Chem. [Online], 27:273-279 (2003).

(Continued)

*Primary Examiner* — Sarah Pihonak
(74) *Attorney, Agent, or Firm* — Adsero IP

(57) ABSTRACT

Provided are methods of using curcuphenol compounds to increase expression of major histocompatibility complex class I (MHC-I) antigen in cells, particularly on the surface of diseased cells such as cancer cells, and thereby increase the immunogenicity of the cells. Also provided are pharmaceutical compositions that comprise curcuphenol compounds and methods of use thereof, for instance, to treat various cancers, alone or in combination with other therapies.

5 Claims, 14 Drawing Sheets

(56) References Cited

OTHER PUBLICATIONS

Wang, Z. et al., "Activation of CXCR4 triggers ubiquitination and down-regulation of major histocompatibility complex class I (MHC-I) on epithelioid carcinoma HeLa cells," Journal of Biological Chemistry, 283(7):3951-3959 (2008).
Wright, A. E. et al., "(+)-curcuphenol and (+)-curcudiol sesquiterpene phenols from shallow and deep water collections of the marine sponge didiscus-flavus," Journal of Natural Products (Lloydia), 50(5):976-978 (1987).
Zagzag, D. et al., "Downregulation of major histocompatibility complex antigens in invading glioma cells: stealth invasion of the brain," Lab Invest. 85(3):328-341 (2005).
Office Action issued for JP Application No. 2019-132434, dated Nov. 4, 2020, 6 pages. English translation.
Office Action issued for CA Application No. 2,930,156, dated Jan. 12, 2021, 4 pages.

\* cited by examiner

*Figure 2A*

Deficiencies of LMP2, LMP7, TAP1 and HLA class I antigens in human tumor cell lines of distinct histology[a]

| Tumor type | Number of samples | Percentage loss or downregulation | | | | | |
|---|---|---|---|---|---|---|---|
| | | LMP2 | LMP7 | TAP1 | TAP2 | HLA I | $\beta_2$m |
| Hodgkin/BL | 8 | 100 | 0 | 100 | 88 | 100 | ND |
| Myeloma | 13 | ND | ND | 13 | 13 | 13 | ND |
| Small-cell lung carcinoma | 6 | 100 | 100 | 100 | 100 | 100 | ND |
| Cervical carcinoma | 7 | 0 | 0 | 0 | 0 | 29 | ND |
| Renal cell carcinoma | 19 | 79 | 74 | 79 | 74 | 34 | 0 |
| Melanoma | 9 | 57 | 78 | 33 | 57 | ND | ND |

[a]Abbreviations: LMP, low-molecular-weight protein; TAP, transporter associated with antigen processing; $\beta_2$m, $\beta_2$-microglobulin; BL, Burkitt's lymphoma; ND, not determined.

Loss or downregulation of TAP1 protein expression in surgically removed tumours

| Tumor type | Number of lesions tested | Primary lesion (%) | | Metastases (%) | |
|---|---|---|---|---|---|
| | | MHC I | TAP | MHC I | TAP |
| Melanoma | 32 | ND | 16 | ND | 22 |
| Colorectal carcinoma | 81 | ND | 14 | ND | ND |
| Cervical carcinoma | 76 | 49 | 49 | ND | ND |
| Breast carcinoma | 63 | 33 | 33 | 44 | 44 |
| Non small-cell lung carcinoma | 93 | 38 | 38 | ND | ND |

ND = not determined
Percentage indicates lesions not stained

*Figure 5*

TAP-1 down-regulation is strongly correlated with disease progression and metastasis
Loss of TAP-1 expression in primary lung cancers
Patients with melanoma tumours negative for TAP-1 expression
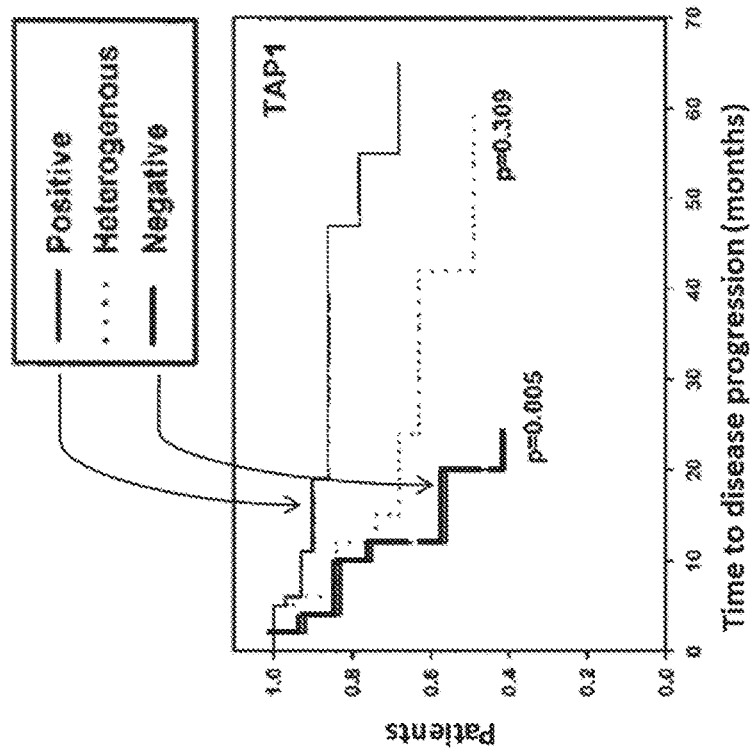
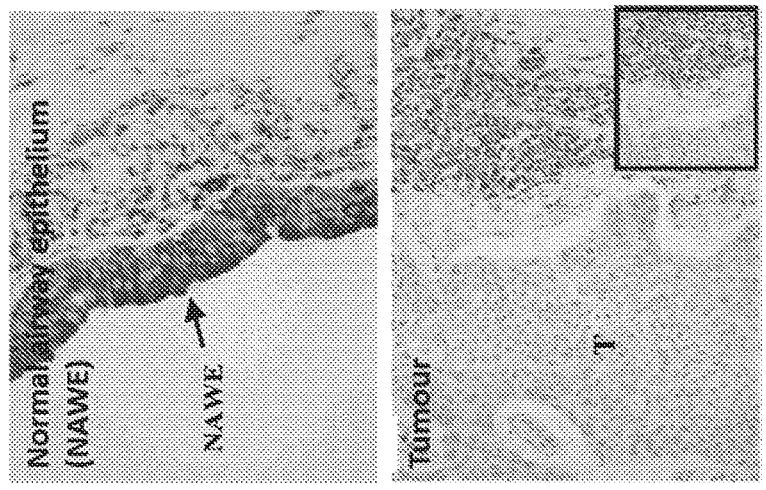
Figure 6

CURCUPHENOL COMPOUNDS FOR INCREASING MHC-I EXPRESSION

CROSS-REFERENCE TO RELATED APPLICATIONS

This application is a Continuation of U.S. application Ser. No. 15/415,291, filed Jan. 25, 2017; which Application is a Continuation of U.S. application Ser. No. 14/548,726, filed Nov. 20, 2014, which claims priority under 35 U.S.C. 119(e) to U.S. Application No. 61/906,817, filed Nov. 20, 2013, the disclosures of which are incorporated herein by reference in their entirety.

BACKGROUND

Technical Field

Embodiments of the present invention relate to the use of curcuphenol compounds for increasing expression of major histocompatibility complex class I (MHC-I) antigen in cells, particularly on the surface of diseased cells such as cancer cells, and thereby increasing the immunogenicity of the cells. Also included are related pharmaceutical compositions and methods of use thereof, for instance, to treat various cancers, alone or in combination with other therapies.

Description of the Related Art

Major histocompatibility complex class I (MHC-I) antigens are found on nearly all nucleated cells of the body. The primary function of this class of major histocompatibility complex (MHC) molecules is to display (or present) peptide fragments of intracellular proteins to cytotoxic T lymphocytes (CTLs). Based on this display, CTLs ignore will healthy cells and attack those displaying MHC-bound foreign or otherwise abnormal peptides, including disease-associated peptide (antigens) such as cancer antigens. Thus, the surface expression of MHC-I molecules plays a crucial role in determining the susceptibility of target cells to CTLs.

Many cancerous cells display down-regulated MHC-I cell surface expression (see, for example, Wang et al., *JBC*. 283: 3951-3959, 2008; Chang et al., *Keio J. Med.* 52:220-9, 2003; Zagzag et al., *Lab Invest.* 85:328-41, 2005; and Hewitt, *Immunology*. 110:163-69, 2003). Reduced MHC-I expression can result at least in part from the down-regulation of multiple factors such as transporters (for example, TAP-1, TAP-2), proteasome components (LMP), and other accessory proteins involved in the antigen presentation and processing pathway. This characteristic may allow cancerous cells to evade immune surveillance and thereby provide a survival advantage against immune activity otherwise designed to eliminate the cells.

Accordingly, there is a need in the art for agents that can increase MHC class I expression in these and other types of diseased cells and thereby improve the ability of the immune system to target such cells for destruction.

BRIEF SUMMARY OF THE INVENTION

Embodiments of the present invention include methods for increasing major histocompatibility complex class I (MHC-I) surface expression in a cell, comprising contacting the cell with a curcuphenol compound. In certain embodiments, MHC-I surface expression is increased by at least about 10% relative to an untreated control cell.

In certain embodiments, the cell (in its untreated state) is characterized by reduced MHC-I surface expression and optionally reduced TAP-1 expression relative to a normal or otherwise healthy cell of the same cell type. In certain embodiments, MHC-I surface expression and optionally TAP-1 expression in the cell is increased to within about 10% of the levels of MHC-I surface expression and optionally TAP-1 expression of the otherwise normal or healthy cell of the same cell type.

In certain embodiments, the cell is a cancer cell. In certain embodiments, the cancer cell is a metastatic cancer cell. In certain embodiments, the cancer cell is selected from one or more of a breast cancer cell, a cervical cancer cell, a prostate cancer cell, a gastrointestinal cancer cell, a lung cancer cell, an ovarian cancer cell, a testicular cancer cell, a head and neck cancer cell, a bladder cancer cell, a kidney cancer cell, a squamous cell carcinoma, a CNS or brain cancer cell, a melanoma cell, a non-melanoma cancer cell, a thyroid cancer cell, a endometrial cancer cell, an epithelial tumor cell, a bone cancer cell, and a hematopoietic cancer cell. In certain embodiments, the bone cancer cell is an osteosarcoma, chondrosarcoma, or a cell of the Ewing Sarcoma Family of Tumors (ESFTs). In certain embodiments, the gastrointestinal cancer cell is an esophageal cancer cell, stomach (gastric) cancer cell, pancreatic cancer cell, liver cancer cell, gallbladder (biliary) cancer cell, small intestinal cancer cell, colorectal cancer cell, anal or rectal cancer cell, or a gastrointestinal carcinoid or stromal tumor. In certain embodiments, the lung cancer cell is an adenocarcinoma, squamous-cell lung carcinoma, small-cell lung carcinoma, or a large-cell lung carcinoma. In certain embodiments, the melanoma is a lentigo maligna, lentigo maligna melanoma, superficial spreading melanoma, acral lentiginous melanoma, mucosal melanomas, nodular melanoma, polypoid melanoma, desmoplastic melanoma, amelanotic melanoma, soft-tissue melanoma, or a uveal melanoma. In certain embodiments, the hematopoietic cancer cell is a lymphoma cell, leukemia cell, or a multiple myeloma cell.

In certain embodiments, the cell is in vitro.

In certain embodiments, the cell is in a subject, and the method comprises administering the curcuphenol compound to the subject. In certain embodiments, the subject has cancer. In certain embodiments, the cancer is characterized by cancer cells (in an untreated state) having reduced MHC-I surface expression and optionally reduced TAP-1 expression relative to non-cancerous cells of the same cell type. In certain embodiments, the cancer cell(s) comprise metastatic cancer cells. In certain embodiments, the metastatic cancer cells (in an untreated state) have reduced MHC-I surface expression and optionally reduced TAP-1 expression relative to non-cancerous cells of the same cell type, or relative to non-metastatic cancer cells of the same cell type.

In certain embodiments, MHC-I surface expression and optionally TAP-1 expression in the cancer cell(s) is increased by at least about 10% relative to a control cell. In certain embodiments, increased MHC-I surface expression and optionally TAP-1 expression increases a CTL-mediated immune response against the cancer cells.

In certain embodiments, the cancer is selected from one or more of breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, bone cancer, and hematopoietic cancer.

In certain embodiments, the lung cancer is osteosarcoma, chondrosarcoma, or a Ewing Sarcoma Family of Tumors (ESFTs). In certain embodiments, the gastrointestinal cancer is esophageal cancer, stomach (gastric) cancer, pancreatic cancer, liver cancer, gallbladder (biliary) cancer, small intestinal cancer, colorectal cancer, anal or rectal cancer, or gastrointestinal carcinoid or stromal tumor. In certain embodiments, the melanoma is lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, or uveal melanoma. In certain embodiments, the hematopoietic cancer is a lymphoma, leukemia, or multiple myeloma. In certain embodiments, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In certain embodiments, the leukemia is chronic lymphocytic leukemia (CLL), hairy cell leukemia, acute lymphoblastic leukemia, myelocytic leukemia, acute myeloid or myelogenous leukemia, or chronic myelogenous leukemia. In certain embodiments, the brain cancer is a glioma, meningioma, pituitary adenoma, vestibular schwannoma, primary CNS lymphoma, neuroblastoma, primitive neuroectodermal tumor (medulloblastoma), or glioblastoma multiforme.

Some methods include administering the curcuphenol compound in combination with an additional cancer therapy. In certain embodiments, the additional cancer therapy selected from one or more of an anti-cancer agent, radiotherapy, surgery, transplantation, photodynamic therapy, symptomatic care, and antibiotic therapy. In certain embodiments, the anti-cancer agent is selected from a small molecule and an antibody. In certain embodiments, the small molecule is a cytotoxic, chemotherapeutic, or anti-angiogenic agent. In certain embodiments, the small molecule cytotoxic, chemotherapeutic, or anti-angiogenic agent is selected from one or more of alkylating agents, anti-metabolites, anthracyclines, anti-tumor antibiotics, platinums, type I topoisomerase inhibitors, type II topoisomerase inhibitors, vinca alkaloids, and taxanes.

In certain embodiments, the small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In certain embodiments, the antibody is selected from one or more of 3F8, 8H9, abagovomab, adecatumumab, afutuzumab, alacizumab (pegol), alemtuzumab, altumomab pentetate, amatuximab, anatumomab mafenotox, apolizumab, arcitumomab, bavituximab, bectumomab, belimumab, bevacizumab, bivatuzumab (mertansine), brentuximab vedotin, cantuzumab (mertansine), cantuzumab (ravtansine), capromab (pendetide), carlumab, catumaxomab, cetuximab, citatuzumab (bogatox), cixutumumab, clivatuzumab (tetraxetan), conatumumab, dacetuzumab, daclizumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Iodine 1-131 monoclonal antibody 81c6 (Neuradiab®) (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, tanezumab, taplitumomab (paptox), tenatumomab, teprotumumab, TGN1412, ticilimumab, trastuzumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

Also included are compositions for use in treating cancer, comprising a pharmaceutically acceptable carrier and a curcuphenol compound or pharmaceutically-acceptable salt thereof. In certain embodiments, the cancer is characterized by cancer cells (in an untreated state) having reduced MHC-I surface expression and optionally reduced TAP-1 expression relative to non-cancerous cells of the same cell type.

Some embodiments include compositions (e.g., pharmaceutical compositions), comprising a pharmaceutically acceptable carrier, an anti-cancer agent, and a curcuphenol compound or pharmaceutically-acceptable salt thereof.

BRIEF DESCRIPTION OF THE FIGURES

FIGS. 2A-2B show the formulae of curcuphenol compounds produced by coupling of curcuphenol with various carboxylic acids.

FIG. 5 shows that TAP-1 and MHC-I are frequently down-regulated in cancer cell lines and surgically removed tumors.

FIG. 6 shows that TAP-1 down-regulation strongly correlates with disease progression and metastasis.

DETAILED DESCRIPTION OF THE INVENTION

Embodiments of the present invention relate to the discovery that curcuphenol compounds can increase MHC-I cell surface expression. In some instances, curcuphenol compounds achieve this effect by increasing the expression of TAP-1 (Transporter associated with Antigen Processing 1), a transporter protein of the MHC-I antigen presentation pathway.

Figure 3:
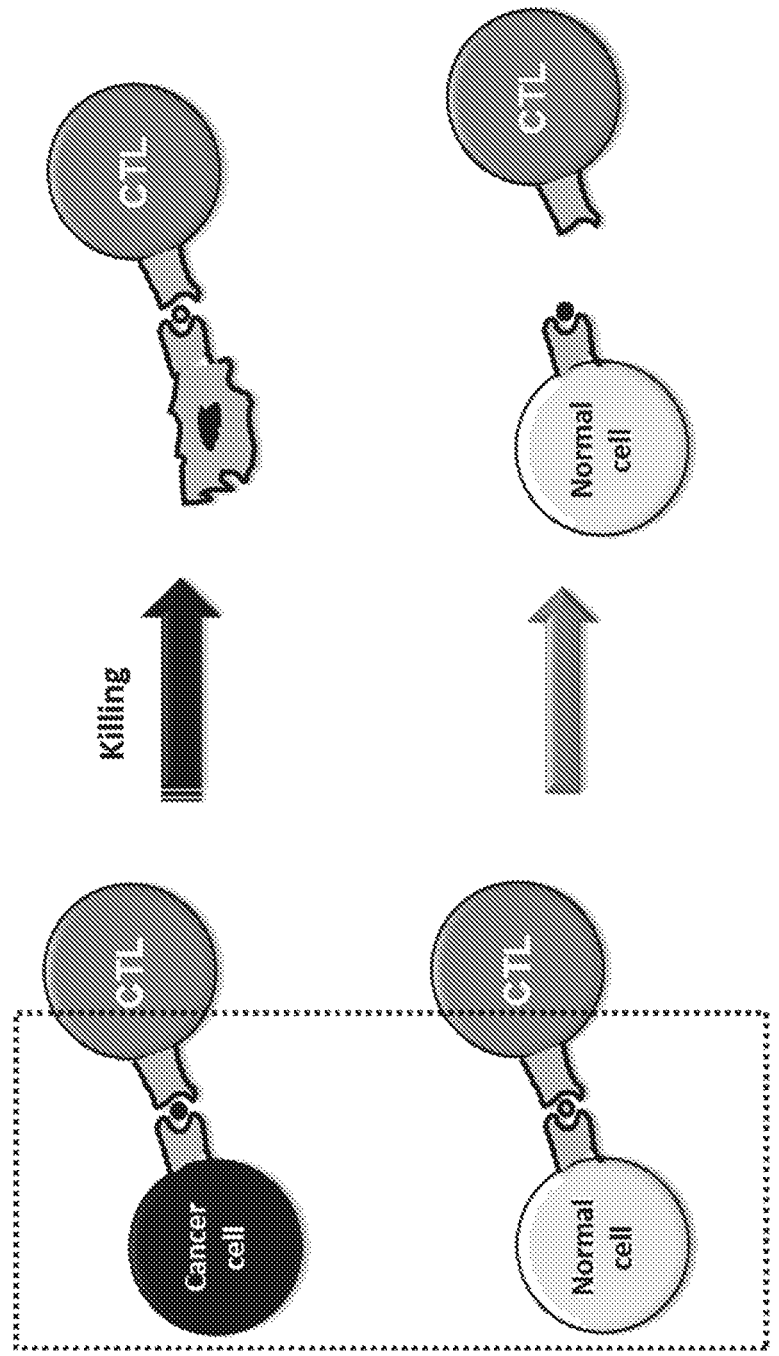
FIG. 3 illustrates the recognition of tumor-associated antigens on cancer cells by cytotoxic T lymphocytes (CTLs).
Figure 4A:
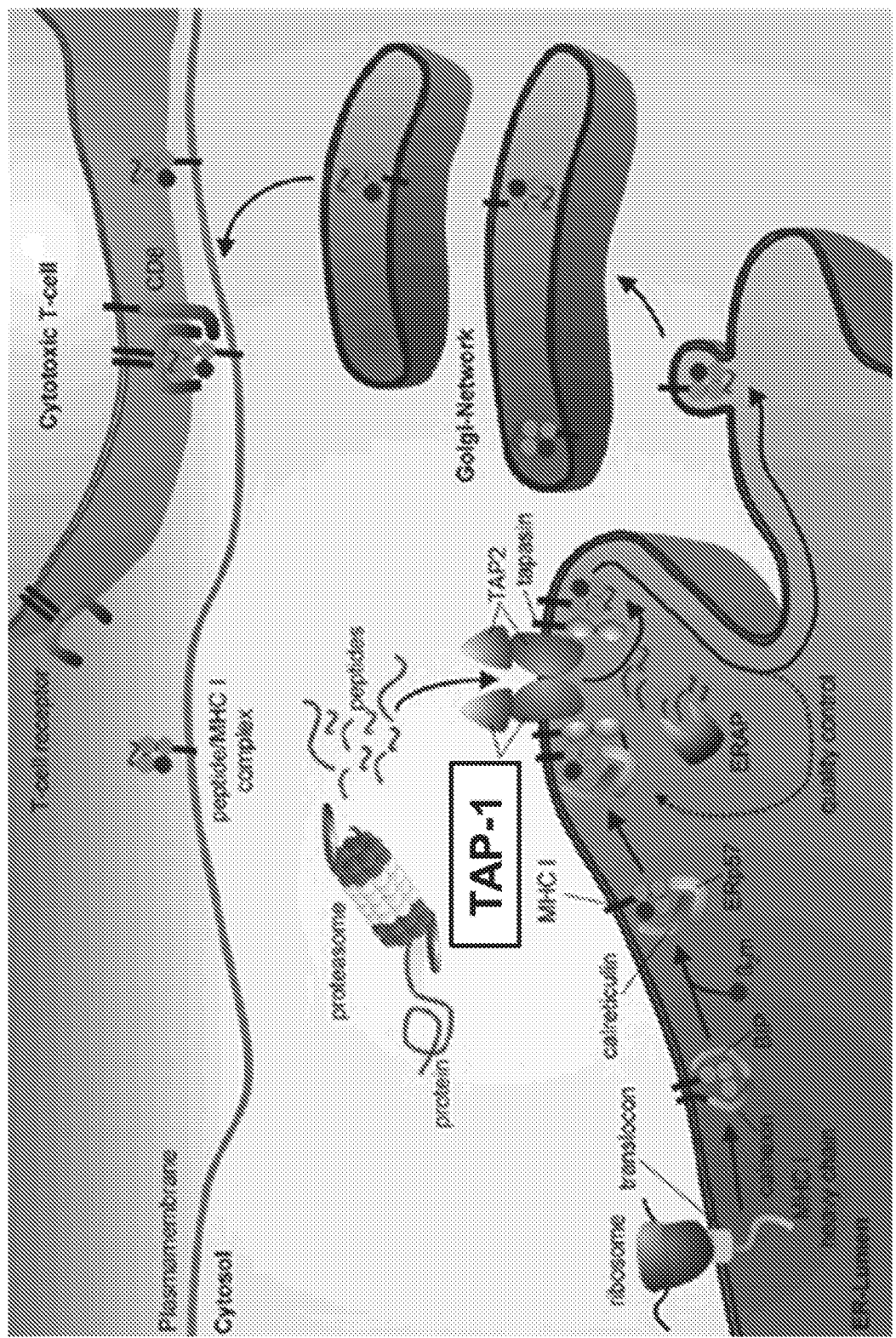
FIG. 4A illustrates the MHC class I antigen presentation pathway, highlighting the role of TAP-1 in the formation of peptide/MHC-I complexes.
Figure 4B:
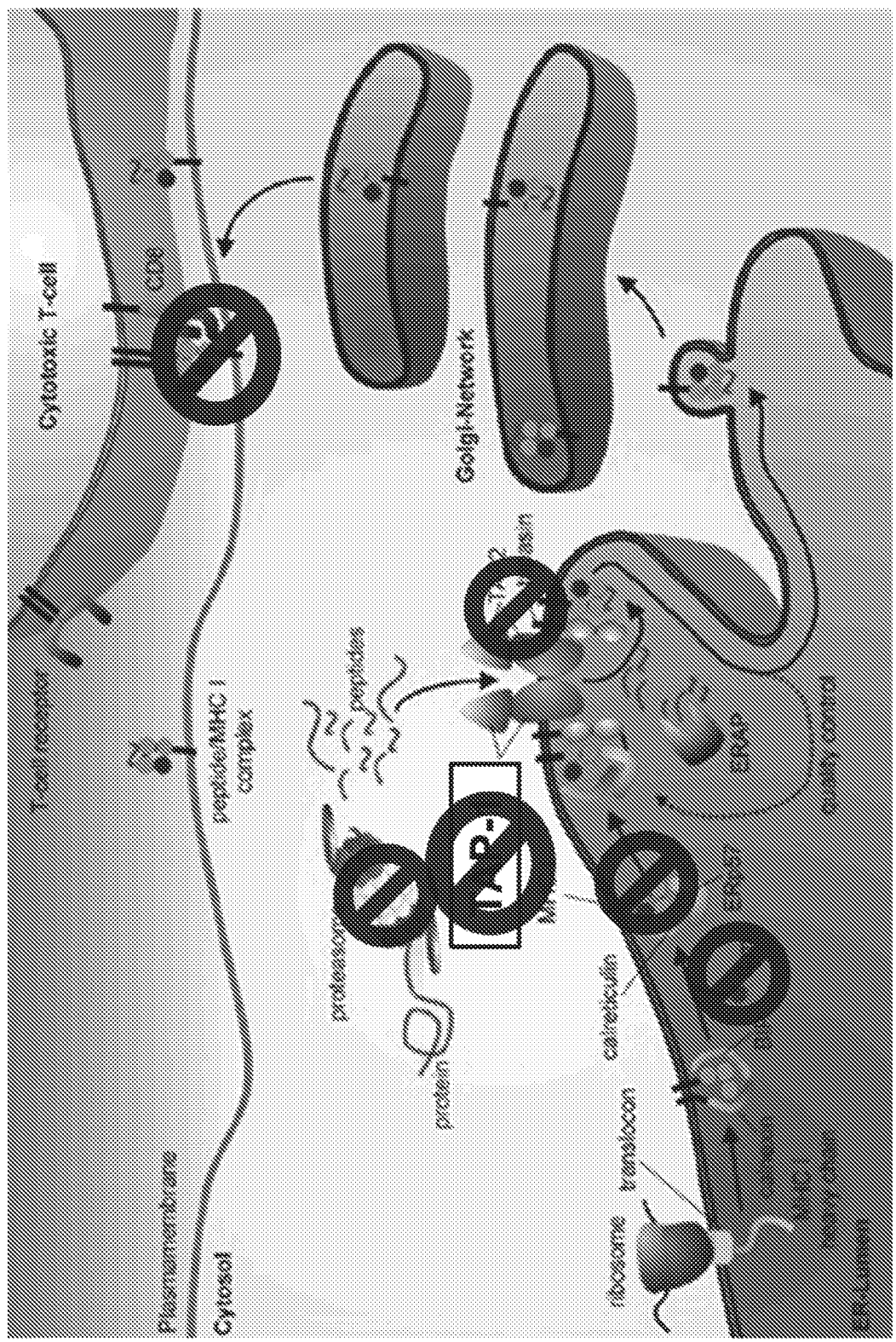
FIG. 4B illustrates the various mechanisms by which cancer cells reduce display of peptide/MHC-I complexes on the cell surface and thereby evade CTL-mediated immune surveillance, including the down-regulation of TAP-1 and TAP-2 transporter proteins and proteasome complexes.

Recognition of MHC-I/peptide complexes is crucial for CTL-mediated immune surveillance of cells (see FIG. 3). Because certain diseased cells such as cancerous cells evade immune surveillance by down-regulating MHC-I cell surface expression, often by down-regulating expression proteins of the antigen presentation pathway such as TAP-1 (see FIGS. 4A-4B and 5-6), curcuphenol compounds may improve CTL-mediated immune activity towards these diseased cells by restoring MHC-I surface expression and presentation of MHC-I/peptide antigen complexes. Curcuphenol compounds may thus find utility in the treatment of diseases associated with reduced MHC-I surface expression and/or TAP-1 expression, including many cancers.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

All publications, patents, and patent applications cited herein are incorporated by reference in their entireties.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points and ranges in between and above 1, e.g., 1.5, 1.6, 1.7. 1.8, etc.) the amount produced by no composition or a control composition, sample, state, or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between) decrease in the amount produced by no composition or a control composition, sample, state, or test subject.

"Optional" or "optionally" means that the subsequently described event or circumstances may or may not occur, and that the description includes instances where said event or circumstance occurs and instances in which it does not.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the curcuphenol compound. As used herein, the term "solvate" refers to an aggregate that comprises one or more molecules of a curcuphenol compound with one or more molecules of solvent. The solvent may be water, in which case the solvate may be a hydrate. Alternatively, the solvent may be an organic solvent. Thus, the curcuphenol compounds may exist as a hydrate, including a monohydrate, dihydrate, hemihydrate, sesquihydrate, trihydrate, tetrahydrate and the like, as well as the corresponding solvated forms. In some instances the curcuphenol compounds may be true solvates, while in other instances the compounds may merely retain adventitious water or be a mixture of water plus some adventitious solvent.

A "pharmaceutical composition" refers to a formulation of a curcuphenol compound and a medium generally accepted in the art for the delivery of the biologically active compound to mammals, e.g., humans. Such a medium includes all pharmaceutically acceptable carriers, diluents or excipients therefor.

The curcuphenol compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms of curcuphenol are also intended to be included.

"Prodrug" is meant to indicate a curcuphenol compound that may be converted under physiological conditions or by solvolysis to a biologically active compound. Thus, the term "prodrug" refers to a metabolic precursor of curcuphenol that is pharmaceutically acceptable. A prodrug may be inactive when administered to a subject in need thereof, but is converted in vivo to an active compound. Prodrugs are typically rapidly transformed in vivo to yield the parent compound, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of curcuphenol may be prepared by modifying functional groups present in the compound in such a way that the modifications are cleaved, either in routine manipulation or in vivo, to the parent compound. Prodrugs include curcuphenol compounds wherein a hydroxy, amino or mercapto group is bonded to any group that, when the prodrug is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in curcuphenol and the like.

Also included are in vivo metabolic products of curcuphenol compounds. Such products may result from, for example, the oxidation, reduction, hydrolysis, amidation, esterification, and the like of the administered compound, primarily due to enzymatic processes. Accordingly, the invention includes curcuphenol compounds produced by a process comprising administering a compound of this invention to a mammal for a period of time sufficient to yield a metabolic product thereof. Such products are typically identified by administering a radiolabelled compound in a detectable dose to an animal, such as rat, mouse, guinea pig, monkey, or to human, allowing sufficient time for metabolism to occur, and isolating its conversion products from the urine, blood or other biological samples.

The "purity" of any given curcuphenol compound or mixture of curcuphenol compounds in a composition may be specifically defined. For instance, certain compositions may comprise a curcuphenol compound that is at least 80, 85, 90, 91, 92, 93, 94, 95, 96, 97, 98, 99, or 100% pure, including all decimals in between, as measured, for example, by high pressure liquid chromatography (HPLC).

"Stable compound" and "stable structure" are meant to indicate a compound that is sufficiently robust to survive isolation to a useful degree of purity from a reaction mixture, and formulation into an efficacious therapeutic agent.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

A "subject," as used herein, includes any animal that exhibits a symptom, or is at risk for exhibiting a symptom, which can be treated or diagnosed with a composition described herein. Suitable subjects (patients) include laboratory animals (such as mouse, rat, rabbit, or guinea pig), farm animals, and domestic animals or pets (such as a cat or dog). Mammals including non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

A "therapeutically effective amount" or "effective amount" includes an amount of a curcuphenol compound which, when administered to a mammal, preferably a human, is sufficient to increase MHC-I surface expression in one or more cells and/or treat any one or more other conditions described herein. The amount of a curcuphenol compound which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

Methods and Pharmaceutical Compositions

The methods and compositions described herein utilize or comprise one or more curcuphenol compounds. Examples of "curcuphenol compounds" include curcuphenol and its enantiomers, stereoisomers, diastereomers, and other stereoisomeric forms, racemates, tautomers, metabolites, and prodrugs that can increase MHC-I surface expression in a cell. Also included are pharmaceutically acceptable salts of the foregoing, including acid and base addition salts.

Curcuphenol is a sesquiterpene phenol isolated from different marine sponges belonging to the genus *Didiscus* (see El Sayed et al., *J Nat Prod.* 65:1547-53, 2002, incorporated by reference in its entirety). It is also referred to as phenol,2-(1,5-dimethyl-4-hexenyl)-5-methyl-, (S)—; Phenol,2-[(1S)-1,5-dimethyl-4-hexenyl]-5-methyl-(9Cl); (+)-Curcuphenol; (S)-(+)-Curcuphenol; and (S)-Curcuphenol.

In certain embodiments, a curcuphenol compound has the following Formula (I-A):

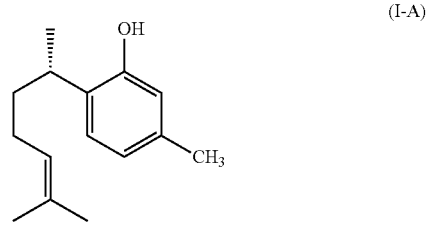 [SMILES: CC(C)=CCC[C@H](C)c1ccc(C)cc1O]

(I-A)

In some embodiments, the curcuphenol compound has the following Formula (I-B):

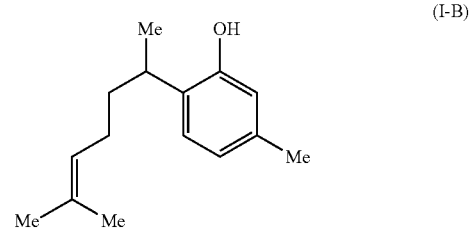 [SMILES: CC(C)=CCCC(C)c1ccc(C)cc1O]

(I-B)

In some embodiments, the curcuphenol compound has the following Formula (II), also referred to as PC-02-113:

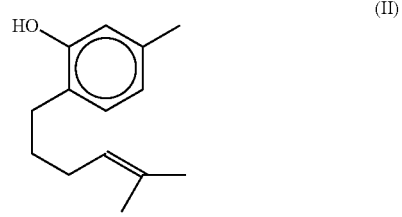

(II)

In some embodiments, the curcuphenol compound has the following Formula (III), also referred to as PC-02-113:

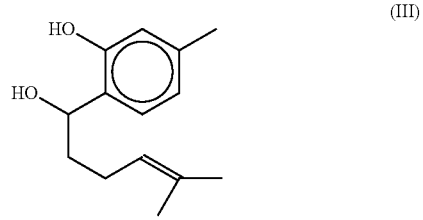

(III)

In some embodiments, the curcuphenol compound has the following Formula (IV), also referred to as PC-02-116:

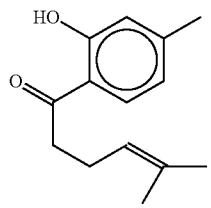

(IV)

In some embodiments, the curcuphenol compound has the following Formula (V), also referred to as PC-02-123:

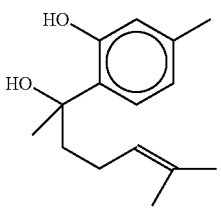

(V)

Figure 1:
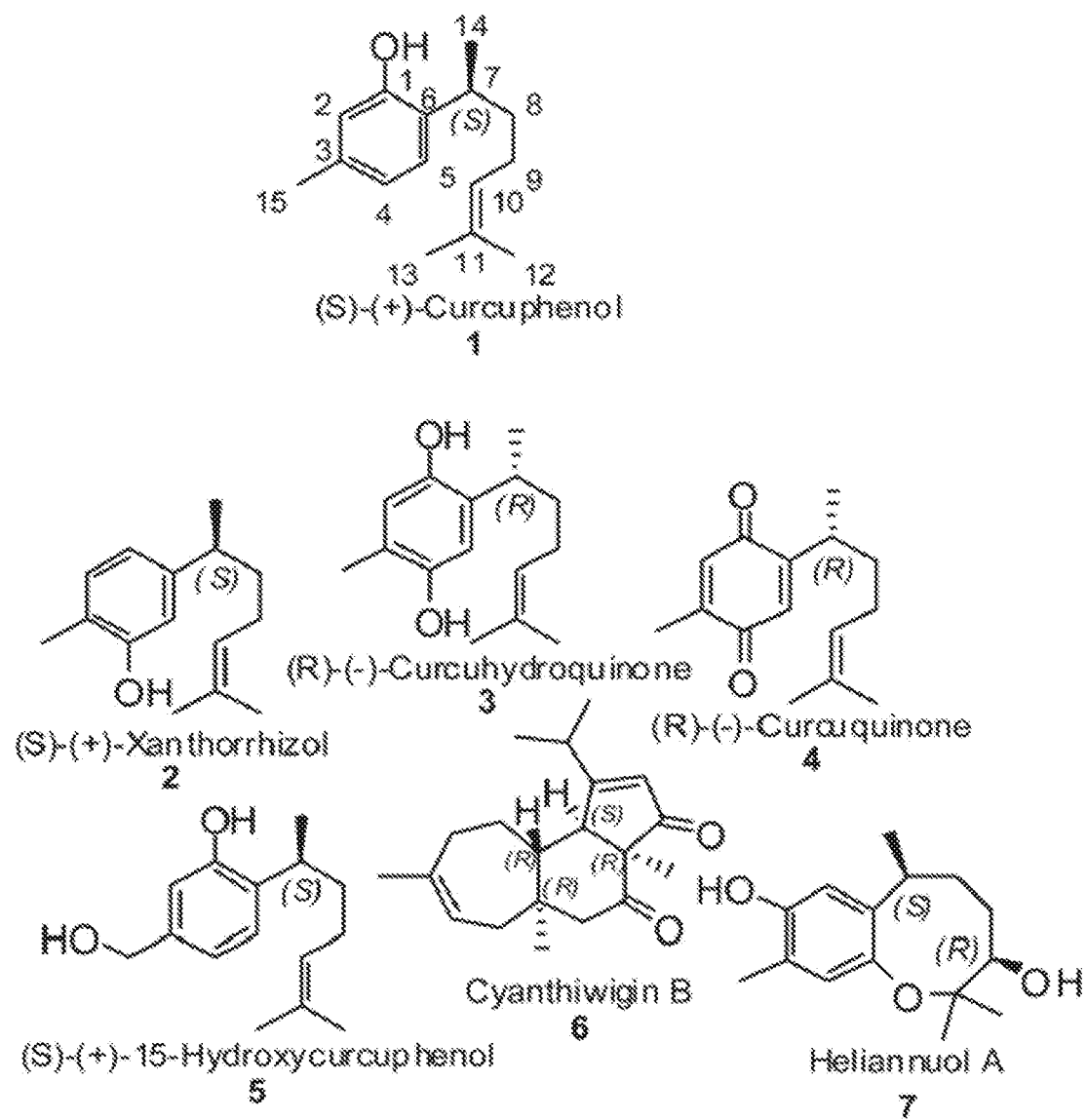
FIG. 1 shows the formulae of (S)-(+)-curcuphenol and various other curcuphenol compounds.
Figure 2A:
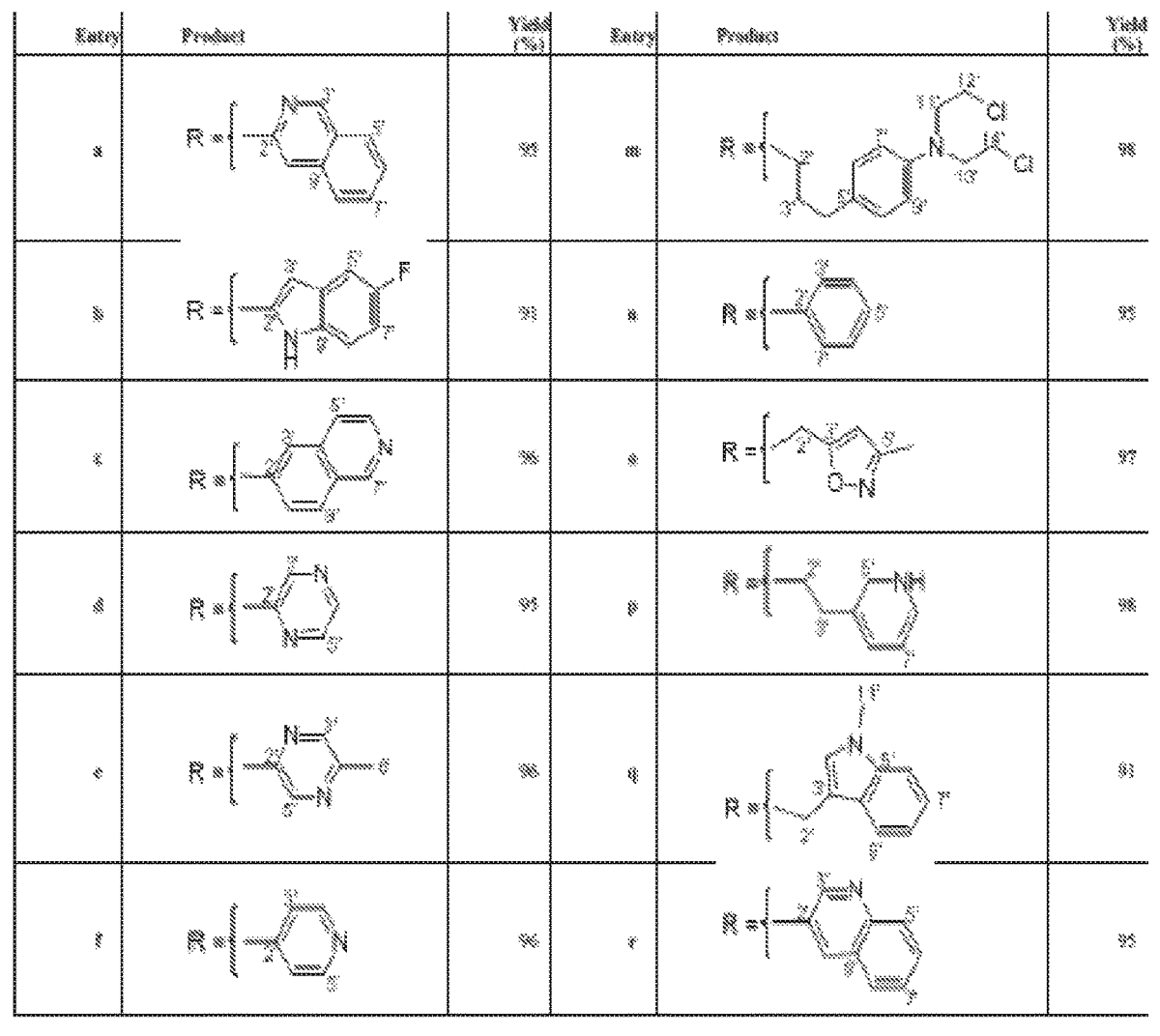
Figure 2B:
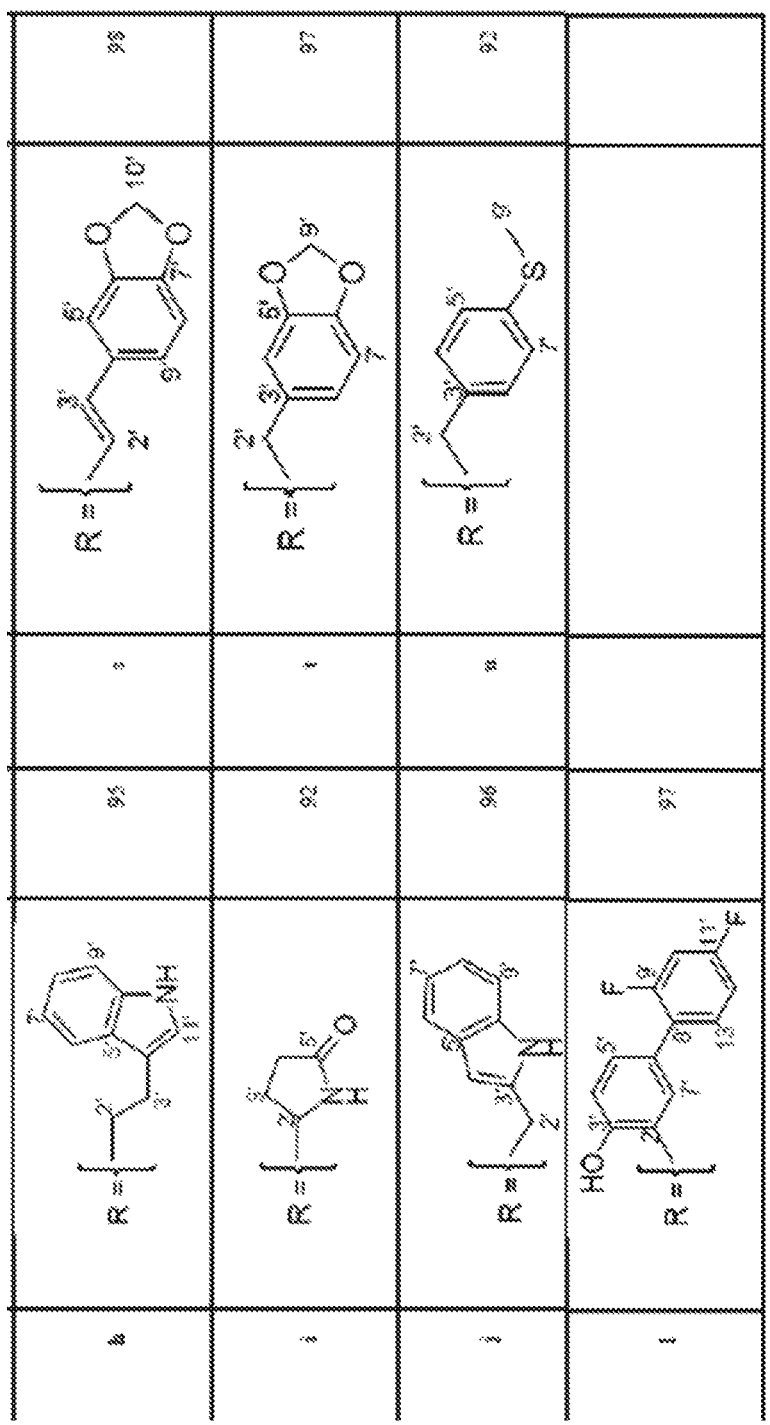
Figure 10:
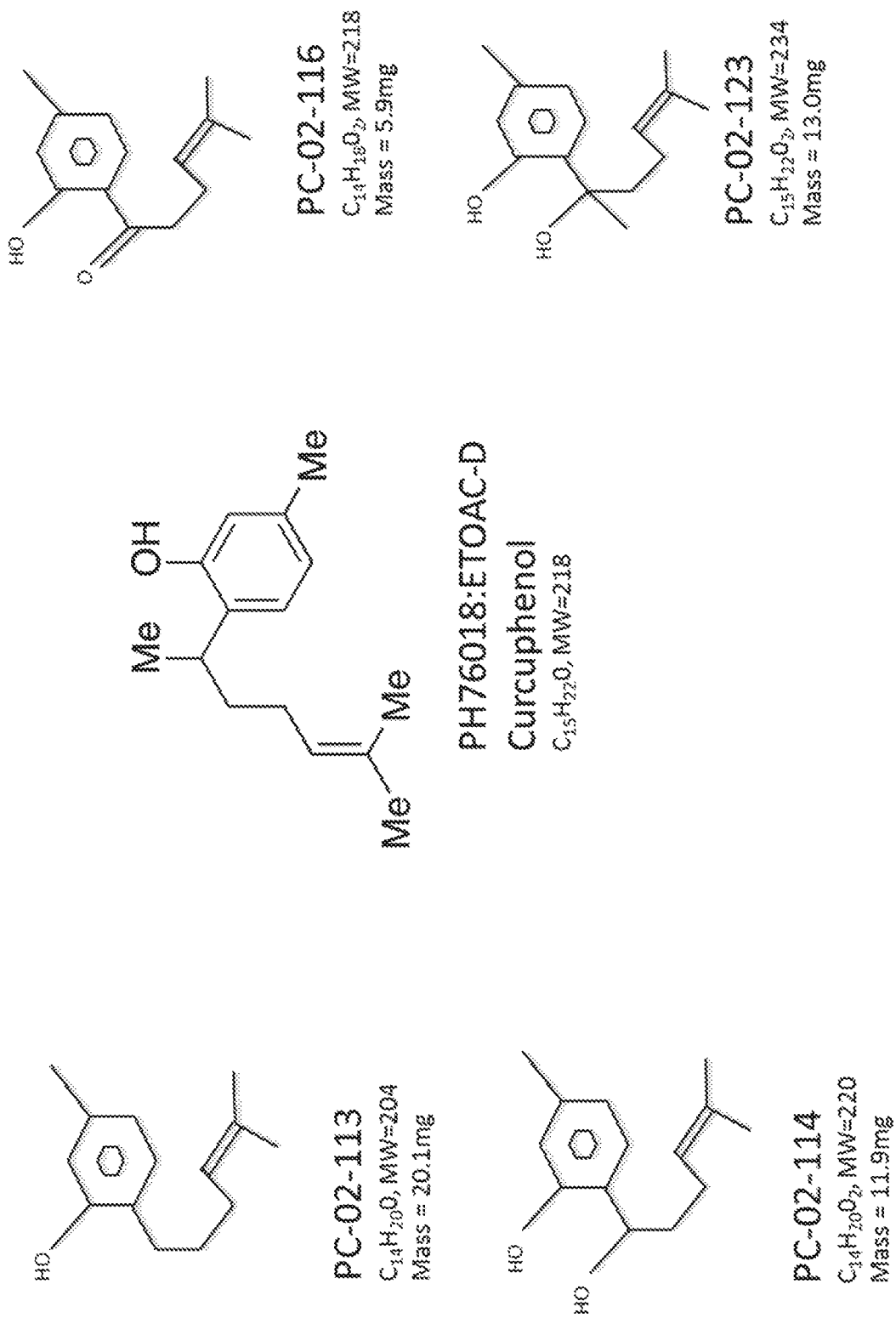
FIG. 10 shows the formulae of the curcuphenol compounds that were tested in the A9 murine tumor cell model (see Example 2).

Specific embodiments employ (S)-(+)-curcuphenol or analogs thereof. For instance, certain embodiments include one or more of (S)-(+)-15-hydroxycurcuphenol, (S)-(+)-12-hydroxycurcuphenol, (S)-(+)-12,15-dihydroxycurcuphenol, (S)-(+)-15-hydroxycurcuphenol-12-al, (S)-(+)-12-carboxy-10,11-dihydrocurcuphenol, (S)-(+)-12-hydroxy-10,11-dihydrocurcuphenol, (S)-(+)-4-[1-(2-hydroxy-4-methyl)phenyl] pentanoic acid (11), (S)-curcuphenol-1alpha-D-glucopyranoside, (S)-(+)-4-nitrocurcuphenol (14), (S)-(+)-2-nitrocurcuphenol, (S)-(+)-curcuphenol-1-O-isonicotinate (see El Sayed et al., 2002, supra). FIG. 1 shows the formulae of (S)-(+)-curcuphenol and various other curcuphenol compounds. FIGS. 2A-2B show the formulae of curcuphenol compounds produced by coupling of curcuphenol with various carboxylic acids. Additional examples of curcuphenol compounds is described, for example, in Gul et al., *Biochim Biophys Acta.* 1770:1513-1519, 2007; Ono et al., *Chem. Pharm. Bull.* 49:1581-1585, 2001; and Plano et al., *Chem Biodivers.* 8:1098-1111, 2011, incorporated by reference in their entireties. FIG. 10 shows the formulae of exemplary curcuphenol compounds, including curcuphenol and analogs thereof. Certain embodiments may employ mixtures of any of the curcuphenol compounds described herein.

In some embodiments, the curcuphenol compound(s) are chemically synthesized. The synthesis of various curcuphenol compounds is described, for example, in El Sayed et al., 2002, supra; Gul et al., 2007, supra; Ono et al., 2001, supra; and Plano et al., 2011, supra.

In certain embodiments, the curcuphenol compound(s) are obtained from marine sponge extracts or terrestrial plant extracts, for example, of the genera *Didiscus, Myrmekioderma, Epipolapsis, Pseudopterogorgia, Elvira,* or *Laisanthaea.* Exemplary species of these marine sponges and terrestrial plants include *Didiscus oxeata, Myrmekioderma styx, Pseudopterogorgia rigida, Elvira biflora,* and *Laisanthaea podocephala.* Certain aspects thus include the administration of marine sponge or terrestrial plant extract(s) that comprise one or more curcuphenol compounds. In some instances, the purity of the curcuphenol compound(s) in the extract is about or at least about 50%, 60%, 70%, 80%, 90%, 95%, 96%, 97%, 98%, 99%, or 100%.

Certain embodiments employ curcuphenol compounds or compositions comprising the same to increase MHC-I expression in a cell, and thereby increase the immunogenicity of the cell—that is, the ability of the immune system (e.g., via interaction with CTLs) to target the cell for destruction. Some embodiments therefore relate to method for increasing major histocompatibility complex class I (MHC-I) surface expression in a cell, comprising contacting the cell with one or more curcuphenol compounds or a composition that comprises the same. In some aspects, MHC-I surface expression is increased by about or at least about 10%, 20%, 30%, 40%, 50%, 60%, 70%, 80%, 90%, 100%, 150%, 200%, 300%, 400%, 500%, 600%, 700%, 800%, 900%, or 1000% or more relative to an untreated control cell.

In some aspects, the curcuphenol compound(s) increase MHC-I surface expression by increasing the expression of Transporter associated with Antigen Processing 1 (TAP-1), a transporter protein of the MHC-I antigen presentation pathway. Hence, in certain aspects, the expression of TAP-1 is increased by about or at least about 10%, 20%, 30%, 40%, 50%, 60%, 70%, 80%, 90%, 100%, 150%, 200%, 300%, 400%, 500%, 600%, 700%, 800%, 900%, or 1000% or more relative to an untreated control cell.

In certain aspects, the cell is a (diseased) cell characterized by reduced MHC-I surface expression (in its untreated state) relative to a non-diseased or otherwise normal or healthy cell of the same cell type. In some aspects, reduced MHC-I surface expression in the diseased cell is associated with or caused by reduced TAP-1 expression. Hence, in some aspects, the cell is a (diseased) cell characterized by reduced TAP-1 expression (in its untreated state) relative to a non-diseased or otherwise normal or healthy cell of the same cell type.

In some aspects, after contacting with one or more curcuphenol compounds, MHC-I surface expression and/or TAP-1 expression in the treated cell is increased to a level that is comparable to the MHC-I surface expression and/or TAP-1 expression of an otherwise normal or healthy cell of the same cell type. For instance, in these and related aspects, MHC-I surface expression and/or TAP-1 expression can be increased to about or within about 50%, 40%, 30%, 20%, 10%, or 5% of the levels of MHC-I surface expression of the otherwise normal or healthy cell of the same cell type.

In certain embodiments, the cell is a cancer or cancerous cell. In specific embodiments, the cancer cell is a metastatic or invasive cancer cell. Examples of cancer cells include breast cancer cell, a cervical cancer cell, a prostate cancer cell, a gastrointestinal cancer cell, a lung cancer cell, an ovarian cancer cell, a testicular cancer cell, a head and neck cancer cell, a bladder cancer cell, a kidney cancer cell (e.g., renal cell carcinoma), a squamous cell carcinoma, a CNS or brain cancer cell, a melanoma cell, a non-melanoma cancer cell, a thyroid cancer cell, a endometrial cancer cell, an epithelial tumor cell, a bone cancer cell, or a hematopoietic cancer cell.

Examples or primary bone cancer cells include osteosarcomas, chondrosarcomas, and cells of the Ewing Sarcoma Family of Tumors (ESFTs). Examples of gastrointestinal cancer cells include esophageal cancer cells, stomach (gastric) cancer cell, pancreatic cancer cells, liver cancer cells, gallbladder (biliary) cancer cells, small intestinal cancer cells, colorectal cancer cells, anal or rectal cancer cells, and gastrointestinal carcinoid or stromal tumors.

Examples of lung cancer cells include adenocarcinomas, squamous-cell lung carcinomas, small-cell lung carcinomas, and large-cell lung carcinomas.

Particular examples of CNS or brain cancer cells include gliomas, meningiomas, pituitary adenomas, vestibular schwannomas, primary CNS lymphomas, neuroblastomas, and primitive neuroectodermal tumors (medulloblastomas). In some embodiments, the glioma is an astrocytoma, oligodendroglioma, ependymoma, or a choroid plexus papilloma. In some aspects, the brain cancer cell is a glioblastoma multiforme. In some embodiments, the glioblastoma multiforme is a giant cell gliobastoma or a gliosarcoma. In particular embodiments, the cancer cell is a metastatic cancer of the CNS, for instance, a cancer cell that has metastasized to the brain. Examples of such cancer cells include, without limitation, metastatic breast cancer cells, metastatic lung cancer cells, metastatic genitourinary tract cancer cells, metastatic gastrointestinal tract cancer cells (e.g., colorectal cancer cells, pancreatic carcinomas), osteosarcomas, melanomas, metastatic head and neck cancer cells, metastatic prostate cancer cells (e.g., prostatic adenocarcinomas), and metastatic lymphomas.

Examples of melanoma cells include those derived from lentigo maligna, lentigo maligna melanomas, superficial spreading melanomas, acral lentiginous melanomas, mucosal melanomas, nodular melanomas, polypoid melanomas, desmoplastic melanomas, amelanotic melanomas, soft-tissue melanomas, and uveal melanomas.

Examples of hematopoietic cancer cells include lymphoma cells, leukemia cells, and multiple myeloma cells. In some instances, the lymphoma cell is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In particular instances, the leukemia cell is chronic lymphocytic leukemia (CLL), hairy cell leukemia, acute lymphoblastic leukemia, myelocytic leukemia, acute myeloid or myelogenous leukemia, or chronic myelogenous leukemia.

In certain embodiments, the cell is in vitro, for example, in tissue culture. Methods of culturing cells including cancer or transformed cells are well-known in the art (see, for example, *Animal Cell Culture* (R. Freshney, ed., 1986); Freshney, R. I. (2005) *Culture of Animal Cells*, a *Manual of Basic Technique*, 5th Ed. Hoboken N.J., John Wiley & Sons).

In certain embodiments, the cell is in a subject, and the method comprises administering the curcuphenol compound or related composition to the subject. For the purposes of administration, the curcuphenol compounds may be administered to a patient or subject as a raw chemical or may be formulated as pharmaceutical compositions. Pharmaceutical compositions generally comprise a curcuphenol compound and a pharmaceutically acceptable carrier, diluent, or excipient. The curcuphenol compound is typically present in the composition in an amount which is effective to treat a particular disease or condition of interest, as described herein, and preferably with acceptable toxicity to the subject. The activity of compound(s) can be determined by one skilled in the art, for example, as described in the Examples below. Appropriate concentrations and dosages can be readily determined by one skilled in the art.

A curcuphenol compound or related composition may be used in a method for treating essentially any disease or other condition in a subject which would benefit from increased surface expression of MHC-I molecules. In particular embodiments, the subject has cancer, and the method comprises treating the cancer by administering one or more curcuphenol compounds to the subject. As illustrated in FIG. 5, TAP-1 is frequently down-regulated in cancer cell lines and surgically removed tumor cells. Without wishing to be bound by any one theory, it is believed that down-regulation of TAP-1 associates with reduced MHC-I surface expression and thus reduced CTL-mediated kill of cancer cells. Restoration of MHC-I, for instance, via restoration of TAP-1 expression, has been shown to increase CTL-mediated killing of cancer cells in vitro and suppression of tumor growth in vivo (see, for example, Zhang et al., 2007, Lou et al., 2007, Lou et al., 2005, Alimonti et al., 2000).

Accordingly, in some aspects, the cancer is characterized by cancer cells having reduced MHC-I surface expression (in an untreated state) and optionally reduced TAP-1 expression (in an untreated state) relative to a non-cancerous cell of the same cell type. In particular aspects, the cancer is characterized by cancer cells having about or less than about 80%, 70%, 60%, 50%, 40%, 30%, 20%, 10%, 5% of the levels of MHC-I surface expression and optionally TAP-1 expression of a non-cancerous cell of the same cell type.

In some aspects, the subject has or is at risk for having a metastatic or invasive cancer. As illustrated in FIG. 6, TAP-1 down-regulation strongly correlates with disease progression and metastasis. Thus, in some aspects, the metastatic cancer is characterized by cancer cells having reduced MHC-I surface expression of MHC-I (in an untreated state) and optionally reduced TAP-1 expression (in an untreated state) relative to a non-cancerous cell of the same cell type, or relative to a non-metastatic cancerous cell of the same cell type. In particular aspects, the cancer is characterized by metastatic cancer cells having about or less than about 80%, 70%, 60%, 50%, 40%, 30%, 20%, 10%, 5% of the levels of MHC-I surface expression and optionally TAP-1 expression of a non-cancerous cell of the same cell type, or of a non-metastatic cancerous cell of the same cell type.

In some aspects, administration of the curcuphenol compound increases MHC-I surface expression and optionally TAP-1 expression in about or at least about 10%, 20%, 30%, 40%, 50%, 60%, 70%, 80%, 90%, or 100% of the cancer cells(s) by about or at least about 10%, 20%, 30%, 40%, 50%, 60%, 70%, 80%, 90%, or 100%, 150%, 200%, 300%, 400%, 500%, 600%, 700%, 800%, 900%, or 1000% or more relative to that of a control cell or population of control cells. In some instances, the control cell(s) are from an untreated state, for example, prior to any treatment, or from one or more earlier-treated states, for example, following a series of administrations or treatments.

In some instances, administration of the curcuphenol compound increases MHC-I surface expression and optionally TAP-1 expression in about or at least about 10%, 20%, 30%, 40%, 50%, 60%, 70%, 80%, 90%, or 100% of the cancer cells(s) to levels comparable to (for example, about or within about 50%, 40%, 30%, 20%, 10%, or 5% of) a reference standard, for example, a reference standard of the average MHC-I surface expression or TAP-1 expression in cells of the same type from healthy (non-cancerous) individuals.

In some embodiments, increased MHC-I surface expression and optionally increased TAP-1 expression increases the immunogenicity of the cancer cells, and thereby increases the immune response against the cancer cells. In some instances, the immune response is a cytotoxic T lymphocyte (CTL)-mediated immune response, and can include, for example, CTL activation, clonal expansion, and increased CTL effector function. Examples of CTL effector functions include the release of release the cytotoxins perforin, granzymes, and granulysin, and increased expression of the CTL surface protein FAS ligand (FasL). In some instances, increased MHC-I surface expression and optionally increased TAP-I expression in the cancer cell(s) increases the CTL-mediated destruction of the cancer cell(s). For solid tumors, administration of one or more curcuphenol compounds can reduce tumor expansion or reduce tumor size, for instance, by about or at least about 10%, 20%, 30%, 40%, 50%, 60%, 70%, 80%, 90%, or 100% relative to an untreated state or an earlier-treated stated.

In some embodiments, the subject has a cancer selected from one or more of breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, bone cancer, or a hematopoietic cancer.

Examples of lung cancers include adenocarcinomas, squamous-cell lung carcinomas, small-cell lung carcinomas, and large-cell lung carcinomas.

Examples or primary bone cancers include osteosarcoma, chondrosarcoma, and the Ewing Sarcoma Family of Tumors (ESFTs).

Examples of gastrointestinal cancers include esophageal cancer, stomach (gastric) cancer, pancreatic cancer, liver cancer, gallbladder (biliary) cancer, small intestinal cancer, colorectal cancer, anal or rectal cancer, and gastrointestinal carcinoid or stromal tumors.

Examples of CNS or brain cancers include primary brain cancers and metastatic brain cancers. Particular examples of brain cancers include gliomas, meningiomas, pituitary adenomas, vestibular schwannomas, primary CNS lymphomas, neuroblastomas, and primitive neuroectodermal tumors (medulloblastomas). In some embodiments, the glioma is an astrocytoma, oligodendroglioma, ependymoma, or a choroid plexus papilloma. In some aspects, the subject has a glioblastoma multiforme. In specific aspects, the glioblastoma multiforme is a giant cell gliobastoma or a gliosarcoma. In particular embodiments, the cancer is a metastatic cancer of the CNS, for instance, a cancer that has metastasized to the brain. Examples of such cancers include, without limitation, breast cancers, lung cancers, genitourinary tract cancers, gastrointestinal tract cancers (e.g., colorectal cancers, pancreatic carcinomas), osteosarcomas, melanomas, head and neck cancers, prostate cancers (e.g., prostate adenocarcinomas), and lymphomas.

Examples of melanomas include lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, and uveal melanoma.

Examples of hematopoietic cancers include lymphomas, leukemias, and multiple myelomas. In some instances, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In particular instances, the leukemia is chronic lymphocytic leukemia (CLL), hairy cell leukemia, acute lymphoblastic leukemia, myelocytic leukemia, acute myeloid or myelogenous leukemia, or chronic myelogenous leukemia.

The use of curcuphenol compounds for treating cancers can be combined with other therapeutic modalities. For example, one or more curcuphenol compounds can be administered to a subject before, during, or after other therapeutic interventions, including symptomatic care, radiotherapy, surgery, transplantation, hormone therapy, immunotherapy, photodynamic therapy, antibiotic therapy, and administration of anti-cancer agents, including any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Examples of anti-cancer agents include small molecules and therapeutic antibodies, among others known in the art. In certain embodiments, the small molecule is a cytotoxic or chemotherapeutic or anti-angiogenic agent. Particular examples include alkylating agents, anti-metabolites, anthracyclines, anti-tumor antibiotics, platinums, type I topoisomerase inhibitors, type II topoisomerase inhibitors, vinca alkaloids, and taxanes. In certain embodiments, the small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In certain embodiments, the antibody is selected from one or more of 3F8, 8H9, abagovomab, adecatumumab, afutuzumab, alacizumab (pegol), alemtuzumab, altumomab pentetate, amatuximab, anatumomab mafenotox, apolizumab, arcitumomab, bavituximab, bectumomab, belimumab, bevacizumab, bivatuzumab (mertansine), brentuximab vedotin, cantuzumab (mertansine), cantuzumab (ravtansine), capromab (pendetide), carlumab, catumaxomab, cetuximab, citatuzumab (bogatox), cixutumumab, clivatuzumab (tetraxetan), conatumumab, dacetuzumab, daclizumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Iodine 1-131 monoclonal antibody 81c6 (Neuradiab®)(with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, tanezumab, taplitumomab (paptox), tenatumomab, teprotumumab, TGN1412, ticilimumab, trastuzumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

As noted above, certain embodiments include pharmaceutical compositions comprising a curcuphenol compound as described herein and a pharmaceutically acceptable carrier. Such pharmaceutical compositions can also comprise one or more additional agents, as described herein, including, for example, anti-cancer agents.

Administration of the curcuphenol compounds, or their pharmaceutically acceptable salts, in pure form or in an appropriate pharmaceutical composition, can be carried out via any of the accepted modes of administration of agents for serving similar utilities. The pharmaceutical compositions can be prepared by combining a curcuphenol compound with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols.

Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: *The Science and Practice of Pharmacy,* 20th Edition (Philadelphia College of Pharmacy and Science, 2000). The composition to be administered will, in any event, contain a therapeutically effective amount of a curcuphenol compound, or a pharmaceutically acceptable salt thereof, for treatment of a disease or condition of interest in accordance with the teachings herein.

A pharmaceutical composition may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a curcuphenol compound such that a suitable dosage will be obtained.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The curcuphenol compounds, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In certain embodiments, a typical dosage of the curcuphenol compound may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

Curcuphenol compounds may also be administered simultaneously with, prior to, or after administration of one or more other therapeutic or biologically active agents, dietary supplements, or any combination thereof. Such combination therapy includes administration of a single pharmaceutical dosage formulation which contains a curcuphenol compound and one or more additional active agents, as well as administration of the curcuphenol compound and each active agent in its own separate pharmaceutical dosage formulation. For example, a curcuphenol compound and the other active agent can be administered to the subject together in a single dosage composition, or each agent administered in separate dosage compositions. Where separate dosage compositions are used, the curcuphenol compounds and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable or reasonably stable compounds.

It will also be appreciated by those skilled in the art that in the process described herein the functional groups of intermediate compounds may need to be protected by suitable protecting groups. Such functional groups include hydroxy, amino, mercapto, and carboxylic acid. Suitable protecting groups for hydroxy include trialkylsilyl or diaryalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of curcuphenol compounds may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all curcuphenol compounds which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

EXAMPLES

Example 1

Curcuphenol-Containing Extracts Induce TAP-1 Promoter Expression and MHC-I Surface Expression Experiments were performed to identify marine sponge extracts that induce TAP-1 promoter expression and MHC-I surface expression in LMD:TAP reporter cells. LMD:TAP reporter cells were derived from metastatic TAP-1 and MHC class I-deficient murine prostate cancer cells and modified to contain a vector that expresses enhanced green fluorescent protein (EGFP) under the control of the TAP-1 promoter.

Figure 7B:
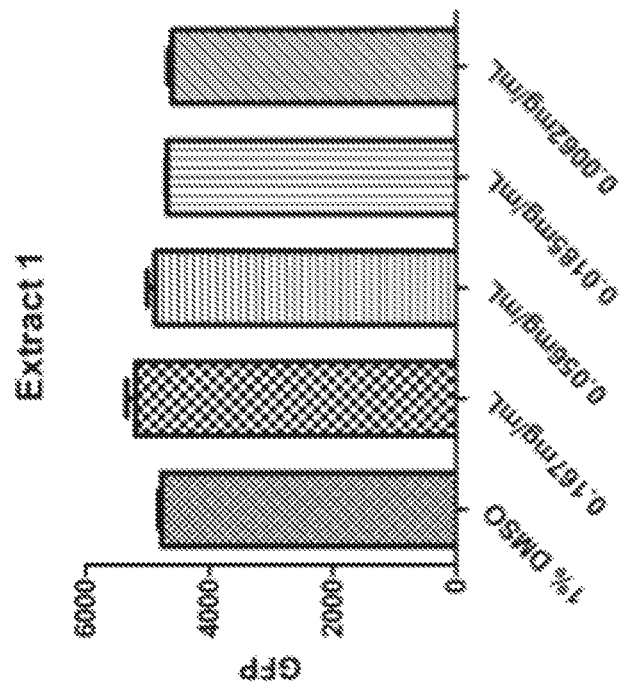
FIGS. 7A-7B show that marine sponge extract 1 increased surface expression of MHC-I (7A) and expression at the TAP-1 promoter (7B, as indicated by EGFP).
Figure 7A:
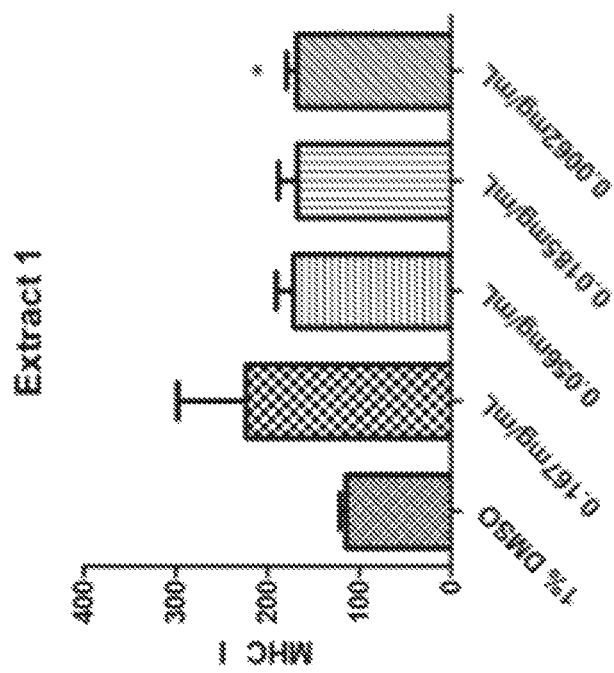
Figure 8A:
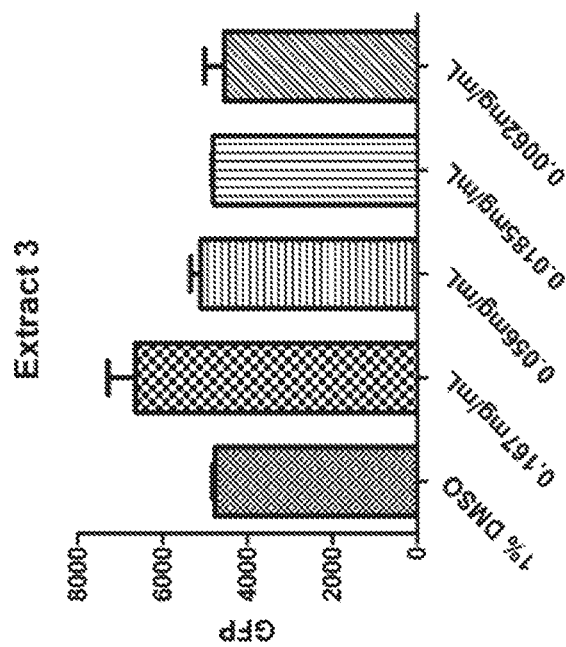
FIGS. 8A-8B show that marine sponge extract 3 increased surface expression of MHC-I (8A) and expression at the TAP-1 promoter (8B, as indicated by EGFP).
Figure 8B:
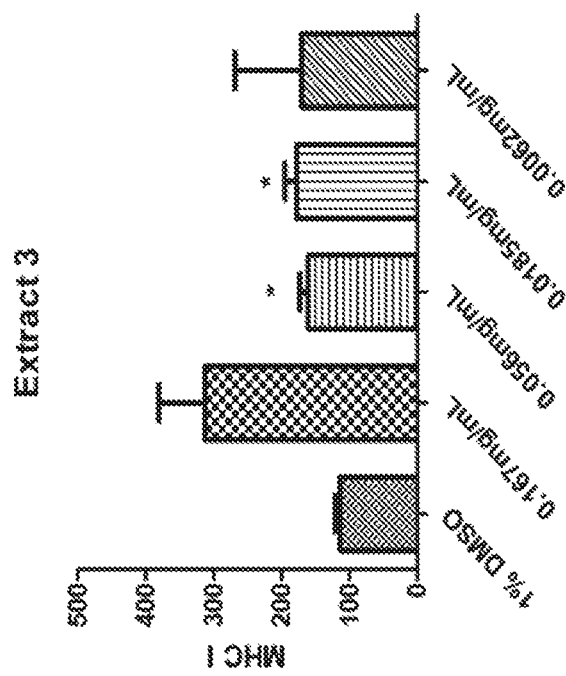
Figure 9B:
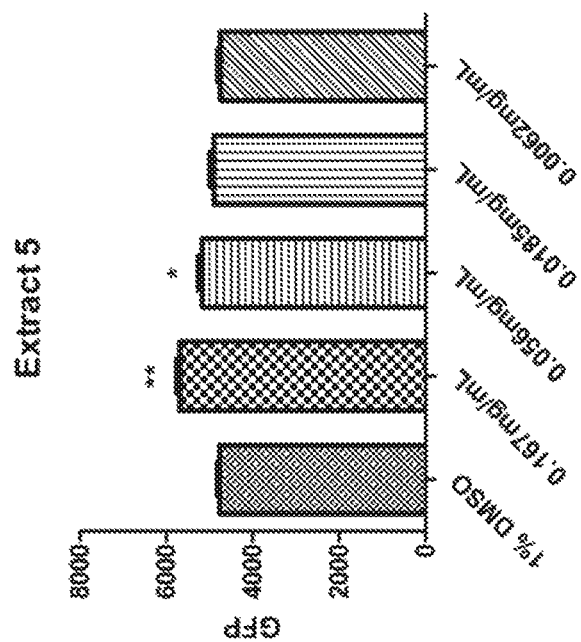
FIGS. 9A-9B show that marine sponge extract 5 increased surface expression of MHC-I (9A) and expression at the TAP-1 promoter (9B, as indicated by EGFP).
Figure 9A:
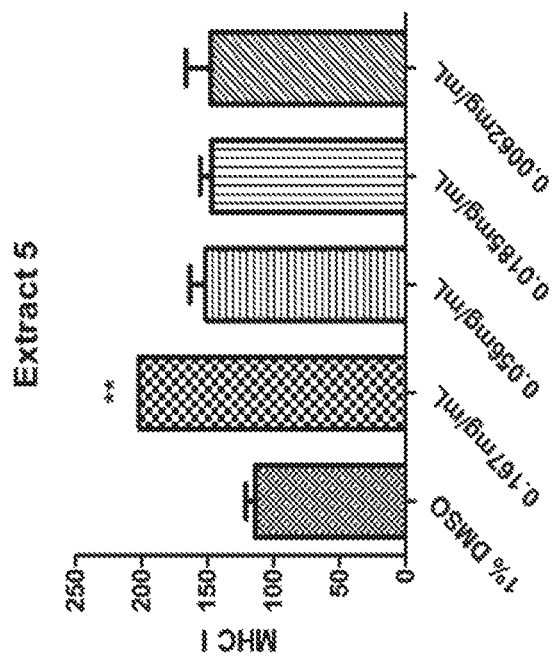

LMD:TAP reporter cells were exposed to marine sponge extracts. Flow cytometry was used to measure expression at the TAP-1 promoter (EGFP expression) and cell surface levels of MHC-I (MAb staining). As shown in FIGS. 7A and 7B, extract 1 increased surface expression of MHC-I (7A) and expression at the TAP-1 promoter (7B, as indicated by EGFP). As shown in FIGS. 8A and 8B, extract 3 increased surface expression of MHC-I (8A) and expression at the TAP-1 promoter (8B, as indicated by EGFP). As shown in FIGS. 9A and 9B, extract 5 also increased surface expression of MHC-I (9A) and expression at the TAP-1 promoter (9B, as indicated by EGFP). Similar results were shown for extract 2.

Extracts 1-3 and 5 were further fractionated into purified extracts and tested by serial dilution to identify the compounds and concentrations with the highest percent activity and the lowest toxicity. The relatively pure extract identified as fraction 1A-b (at 0.018 mg/mL) displayed significant ability to increase both TAP-1 promoter activity and MHC-I expression (110% activity relative to IFN-γ positive control; % activity=x–μn/μp–μn, where x is the average GFP fluorescence intensity, and pn and pp represent the average of the DMSO negative control and IFN-γ positive control), and minimal toxicity (cell numbers up to 20% below the average cell number of the negative DMSO control minus 3 standard deviation). The active compound in this extract was identified as curcuphenol.

Example 2

Curcuphenol and Analogs Induce MHC-I Expression in Lung Tumor Cells

Curcuphenol and four curcuphenol analogs (see FIG. 10) were synthesized and tested for the ability to increase MHC-I expression in TC1/A9 murine lung tumor cells. Toxicity was also measured by propidium iodide (P1) exclusion.

Figure 11A:
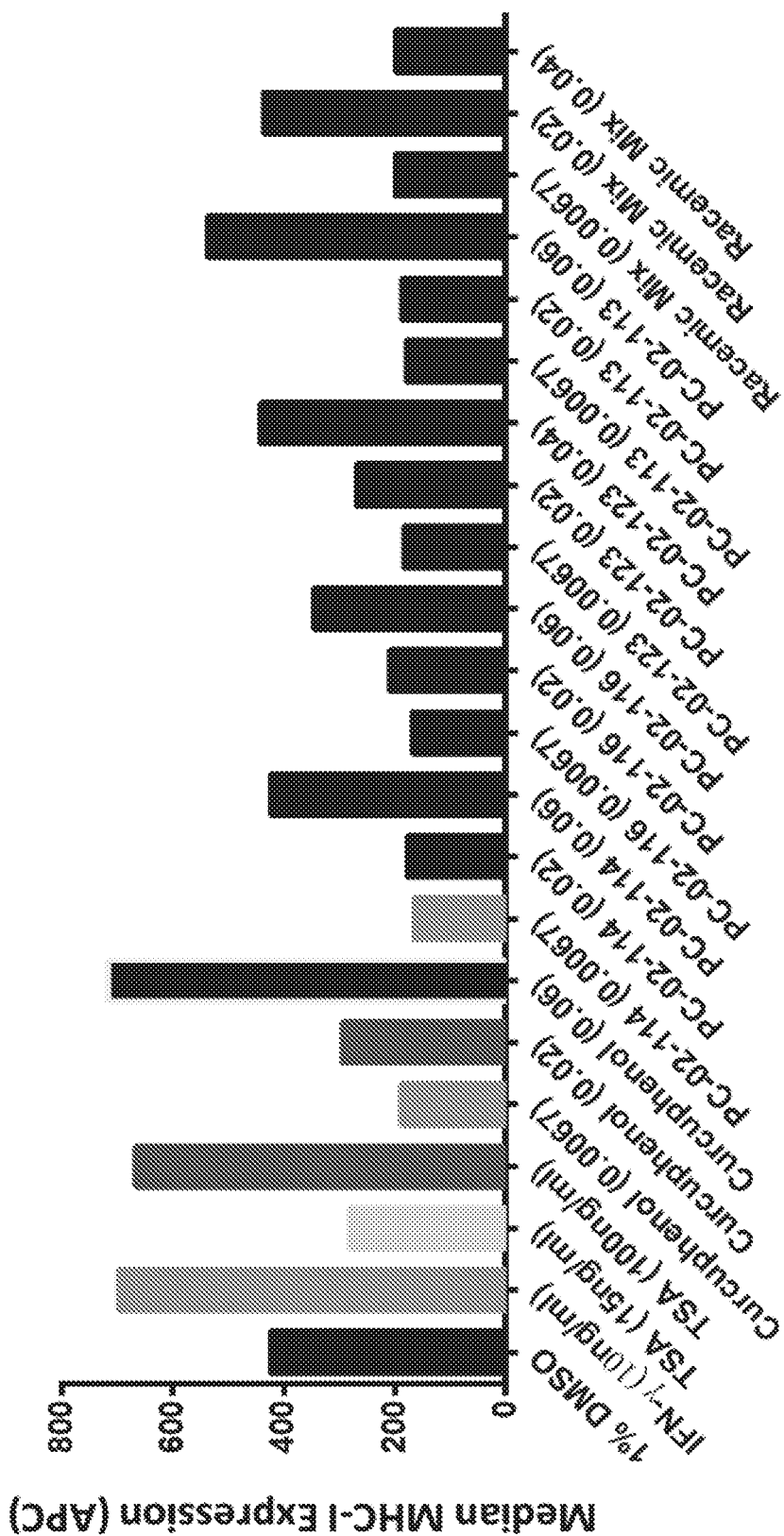
FIG. 11A shows the induction of MHC-I expression in A9 cells by curcuphenol compounds.
Figure 11B:
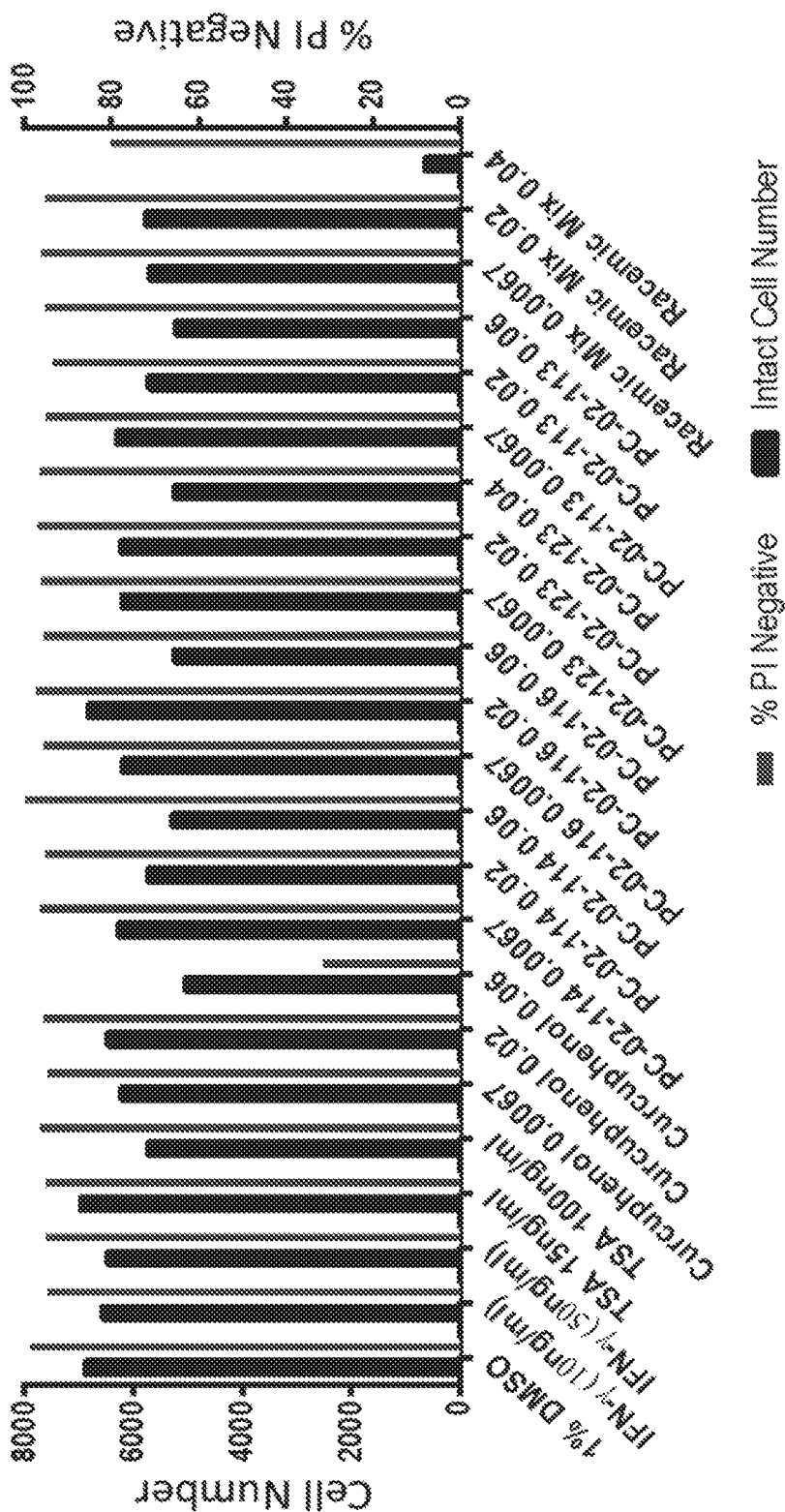
FIG. 11B shows the results of cell toxicity studies in A9 cells, as measured by PI exclusion and intact cell number.

The results are shown in FIGS. 11A and 11B. FIG. 11A shows that curcuphenol and the analog PC-02/113 had the best activity by significantly increasing MHC-I expression relative to controls. FIG. 11B shows that these compounds also had acceptable levels of toxicity, with PC-02/113 showing the best combination of activity and toxicity.

Example 3

Testing of Curcuphenol Compound in Mouse Tumor Model

The compound PC-02-113 is selected for further testing in animal studies. This compound is tested for its Maximum Tolerable Dose (MTD) in mice. Single intraperitoneal (IP) doses are administered as shown in Table E1 below, followed by clinical observation for 14 days.

TABLE E1

Maximum Tolerable Dose Study Plan

| Agent | Dose | # Mice (C57Bl/6) |
|---|---|---|
| Curcuphenol, PC-02-113 (10× less) | 0.05 mg/kg | 3 |
| Curcuphenol, PC-02-113 | 0.5 mg/kg | 3 |
| Curcuphenol, PC-02-113 (10× more) | 5.0 mg/kg | 3 |
| Vehicle alone | n/a | 3 |

This compound is also tested for its anti-tumor effects in mice injected with A9 tumor cells as shown in Table E2 below.

TABLE E2

Anti-Tumor Effect Study Plan

| Agent | Dose | # Mice (C57Bl/6) |
|---|---|---|
| [A9 + vect] | n/a | 8 |
| [A9 + vect] + [Curcuphenol, PC-02-113] | As determined by MTD | 8 |
| [A9 + vect] + [TSA] | 0.5 mg/kg | 8 |

The curcuphenol compound is administered 3 times a week (M, W, F) for four weeks by intraperitoneal (IP) injection. Tumors are measured 3 times a week: tumors from 4 mice/group are collected for immunohistochemistry (IHC) analysis, and tumors from the other 4 mice/group are collected for analysis of tumor-infiltrating lymphocytes (TIL). Lymph nodes, liver, brain, adrenal glands, spleen and blood are collected from mice and analyzed at the end of the study.

The invention claimed is:
1. A method for treating cancer, comprising administering a curcuphenol compound to a subject having cancer, wherein said curcuphenol compound is

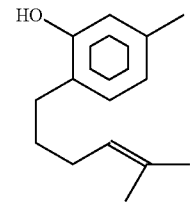

or a pharmaceutically acceptable salt thereof; and wherein said cancer is carcinoma.
2. The method of claim 1, wherein the cancer is characterized by cancer cells in an untreated state having reduced MHC-1 surface expression and optionally reduced TAP-1 expression relative to non-cancerous cells of the same cell type.
3. The method of claim 2, wherein MHC-1 surface expression and optionally TAP-1 expression in the cancer cell(s) is increased by at least about 10% relative to a control cell wherein optionally increased MHC-1 surface expression and optionally TAP-1 expression increases a CTL-mediated immune response against the cancer cells after administration of said curcuphenol compound.
4. The method of claim 1, wherein the cancer is carcinoma of the lung or prostate.
5. The method of claim 1, further comprising administering an additional cancer therapy wherein optionally the additional cancer therapy selected from one or more of an anti-cancer agent, radiotherapy, surgery, transplantation, photodynamic therapy, symptomatic care, and antibiotic therapy wherein optionally the anti-cancer agent is selected from a small molecule and an antibody wherein optionally the small molecule is a cytotoxic, chemotherapeutic, or anti-angiogenic agent wherein optionally the small molecule cytotoxic, chemotherapeutic, or anti-angiogenic agent is selected from one or more of alkylating agents, anti-metabolites, anthracyclines, anti-tumor antibiotics, platinums, type I topoisomerase inhibitors, type II topoisomerase inhibitors, vinca alkaloids, and taxanes wherein optionally the small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine, tetrabenazine, bexarotene, glatirimer acetate, fingolimod, and mitoxantrone, including pharmaceutically acceptable salts and acids thereof, where optionally the antibody is selected from one or more of 3F8, 8H9, abagovomab, adecatumumab, afutuzumab, alacizumab, alemtuzumab, altumomab pentetate, amatuximab, anatumomab mafenotox, apolizumab, arcitumomab, bavituximab, bectumomab, belimumab, bevacizumab, bivatuzumab (mertansine), brentuximab vedotin, cantuzumab, cantuzumab, capromab, carlumab, catumaxomab, cetuximab, citatuzumab, cixutumumab, clivatuzumab, conatumumab, dacetuzumab, daclizumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab, girentuximab, glembatumumab, ibritumomab tiuxetan, icrucumab, igovomab, indatuximab ravtansine, intetumumab, inotuzumab ozogamicin, ipilimumab, iratumumab, labetuzumab, lexatumumab, lintuzumab, lorvotuzumab, lucatumumab, lumiliximab, mapatumumab, matuzumab, milatuzumab, mitumomab, mogamulizumab, moxetumomab (pasudotox), nacolomab (tafenatox), naptumomab, narnatumab, necitumumab, nimotuzumab, nivolumab, Iodine 1-131 monoclonal antibody 81c6, NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, tanezumab, taplitumomab, tenatumomab, teprotumumab, TGN1412, ticilimumab, trastuzumab, tremelimumab, tigatuzumab, TNX-650, tositumomab, TRBS07, tucotuzumab, ublituximab, urelumab, veltuzumab, volociximab, votumumab, and zalutumumab, including antigen-binding fragments thereof.

\* \* \* \* \*